[12] United States Patent
Biscay et al.

(10) Patent No.: US 10,687,928 B2
(45) Date of Patent: Jun. 23, 2020

(54) APPARATUS FOR VAGINAL PENETRATION OF ANIMALS COMPRISING A VIEWING SYSTEM, IN PARTICULAR FOR LOCATING THE CERVIX OF THE UTERUS

(71) Applicant: IMV TECHNOLOGIES, Saint Ouen sur Iton (FR)

(72) Inventors: Jean Arnaud Biscay, Saint Palais (FR); Virginie Rosa, Biarritz (FR); Esclarmonde De Riberolles, Meillon (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 301 days.

(21) Appl. No.: 15/522,822

(22) PCT Filed: Oct. 28, 2015

(86) PCT No.: PCT/FR2015/052909
§ 371 (c)(1),
(2) Date: Apr. 28, 2017

(87) PCT Pub. No.: WO2016/066962
PCT Pub. Date: May 6, 2016

(65) Prior Publication Data
US 2017/0319317 A1 Nov. 9, 2017

(30) Foreign Application Priority Data
Oct. 28, 2014 (FR) ...................... 14/60352

(51) Int. Cl.
A61D 19/02 (2006.01)
A61B 1/00 (2006.01)
(Continued)

(52) U.S. Cl.
CPC ........ *A61D 19/027* (2013.01); *A61B 1/00016* (2013.01); *A61B 1/00032* (2013.01);
(Continued)

(58) Field of Classification Search
CPC ............ A61D 19/027; A61D 2090/306; A61B 2090/306; A61B 2010/0074;
(Continued)

(56) References Cited

U.S. PATENT DOCUMENTS 2,942,603 A   6/1960 Geyer
4,474,576 A * 10/1984 Gobby ................. A61D 19/027
                                                      604/115

(Continued)

FOREIGN PATENT DOCUMENTS

EP   2529695 A2   12/2012
FR   2690072 A1   10/1993
(Continued)

*Primary Examiner* — Christine H Matthews
*Assistant Examiner* — Joshua Daryl D Lannu
(74) *Attorney, Agent, or Firm* — Browdy and Neimark, P.L.L.C.

(57) ABSTRACT

An appliance for vaginal penetration includes a grip, the appliance being designed to receive a working tool, especially an insemination gun that passes through the grip. A guiding tube extends the grip in order to form a compact assembly, the guiding tube being designed so as to receive the front tip of the working tool therein and receiving a video viewing device such as an endoscopy-type tube including a lighting element on the front end thereof, the appliance for vaginal penetration including an electronic cell receiving the video images, provided with a device for transmitting images to a remote screen.

23 Claims, 3 Drawing Sheets

(51) Int. Cl.

| | | |
|---|---|---|
| *A61M 31/00* | (2006.01) | |
| *A61B 10/00* | (2006.01) | |
| *A61B 7/02* | (2006.01) | |
| *A61B 1/04* | (2006.01) | |
| *A61B 1/018* | (2006.01) | |
| *A61B 1/12* | (2006.01) | |
| *A61B 1/303* | (2006.01) | |
| *A61B 90/00* | (2016.01) | |
| *A61B 90/30* | (2016.01) | |

(52) U.S. Cl.
CPC ...... *A61B 1/00066* (2013.01); *A61B 1/00124* (2013.01); *A61B 1/00154* (2013.01); *A61B 1/018* (2013.01); *A61B 1/04* (2013.01); *A61B 1/128* (2013.01); *A61B 1/303* (2013.01); *A61B 7/023* (2013.01); *A61B 10/0045* (2013.01); *A61M 31/00* (2013.01); *A61B 90/361* (2016.02); *A61B 2010/0074* (2013.01); *A61B 2090/306* (2016.02); *A61B 2090/309* (2016.02); *A61B 2090/3614* (2016.02); *A61M 2210/1475* (2013.01)

(58) Field of Classification Search
CPC ..... A61B 10/0045; A61B 7/023; A61B 1/303; A61B 1/128; A61B 1/018; A61B 1/00154; A61B 1/00124; A61B 1/00066; A61B 1/00032; A61B 1/00016; A61B 1/04; A61B 2090/3614; A61B 2090/309; A61B 90/361; A61M 31/00; A61M 2210/1475; A61M 2010/0074
See application file for complete search history.

(56) References Cited

U.S. PATENT DOCUMENTS

| | | | | |
|---|---|---|---|---|
| 2002/0151764 | A1* | 10/2002 | Erwin | A61D 19/027 600/35 |
| 2003/0004397 | A1* | 1/2003 | Kameya | A61B 1/05 600/101 |
| 2005/0049509 | A1* | 3/2005 | Mansour | A61B 5/1076 600/476 |
| 2005/0255039 | A1* | 11/2005 | Desai | A61K 9/0034 424/1.11 |
| 2007/0106247 | A1* | 5/2007 | Burnett | A61F 7/12 604/508 |
| 2008/0058605 | A1* | 3/2008 | Sorensen | A61B 1/32 600/208 |
| 2011/0105850 | A1* | 5/2011 | Voegele | A61B 1/303 600/207 |
| 2011/0282135 | A1* | 11/2011 | Waybright | A61D 19/027 600/35 |
| 2013/0066304 | A1* | 3/2013 | Belson | A61B 17/00234 606/1 |
| 2014/0200402 | A1* | 7/2014 | Snoke | A61B 17/42 600/104 |

FOREIGN PATENT DOCUMENTS

| | | | | |
|---|---|---|---|---|
| FR | 2908038 A | 5/2008 | | |
| FR | 2908038 A1 * | 5/2008 | ........... | A61D 19/027 |
| JP | 03275053 A | 12/1991 | | |
| JP | 2010213948 A | 9/2010 | | |
| WO | 9714365 A1 | 4/1997 | | |
| WO | WO-9714365 A1 * | 4/1997 | ........... | A61D 19/027 |
| WO | 0205727 A1 | 1/2002 | | |
| WO | WO-0205727 A1 * | 1/2002 | ........... | A61D 17/002 |

* cited by examiner

APPARATUS FOR VAGINAL PENETRATION OF ANIMALS COMPRISING A VIEWING SYSTEM, IN PARTICULAR FOR LOCATING THE CERVIX OF THE UTERUS

The present invention concerns an apparatus for assisting in, or for, vaginal penetration, or an adaptor for assisting in, or for, vaginal penetration, for animals, enabling various operations to be performed, as well as methods of use of that apparatus.

In order to perform artificial insemination of animals such as ovine, caprine, porcine or bovine livestock, a known apparatus, presented in particular by the document FR-A-1-2690072, comprises an elongate gun having a front tip enabling the operator to penetrate the vagina to reach the cervix of the uterus, and inject into that uterus as closely as possible to the fallopian tubes the liquid semen contained in a straw or in a capsule.

However, for certain animals, in particular for bovine livestock such as heifers never having calved, the passage through the vagina is difficult to perform since it comprises numerous tight folds which are difficult to pass, and the entry of the cervix of the uterus is difficult to locate, as well as to pass since very narrow.

During this operation which may take more or less time to carry out according to the familiarity of the user and the specificity of the animal, the latter may become irked by the pricking of the tip of the gun on sensitive internal tissues, which makes the operation more difficult and uncomfortable, with constraints for the livestock farmer as well as a greater risk of error.

There is thus greater risk of performing an injection of semen with no result, which leads to lost time, and wasting of the semen having a certain cost.

Furthermore, recent European regulations authorize livestock farmers to perform inseminations by themselves, without passing via a specialist organization, which increases the interest for simple and effective apparatuses enabling these operations to be performed with a good level of reliability, comfort and safety, by staff carrying out these operations occasionally.

The present invention is in particular directed to avoiding these drawbacks of the prior art.

To at end it provides an apparatus for vaginal penetration comprising a handling shaft provided to receive a work tool in particular an insemination gun passing through the shaft, characterized in that it comprises a guide tube extending the shaft to form a compact assembly, the guide tube receiving internally the front tip of the work tool as well as a video viewing means such as a tube of endoscope type comprising lighting at its front end, the apparatus for vaginal penetration comprising an electronic cell receiving the video images and having available means for transmitting the images to a remote screen.

Of course, the work tool may also be a syringe for injection of an antibiotic or any other type of gun or syringe for injection, by vaginal penetration, of any substance, for example semen, antibiotic or any other product.

An advantage of this apparatus for vaginal penetration is that on account of the view on the remote screen which is not subjected to the movements of the animal, enabling a clear and stable image to be obtained, it is possible to manipulate the compact shaft easily which thus provides a good grip, in order to facilitate the insertion of the end of the guide tube between the folds or narrow regions, to position in particular the tip of the gun at the precise location ensuring the best results for the operation.

Another advantage of this apparatus is to limit or avoid lesions which may be caused by the fineness of the existing tool, in particular the insemination gun. This is all the more important during manipulations by an occasional user.

Furthermore the remote screen is not at risk of being soiled by the animal's dejections. The operator can thus work in a relaxed and rapid manner, without being hindered too much by movements of the animal's tail, and without causing it great stress. The user can thus manipulate the assembly of the apparatus with a single hand. The design of this apparatus also provides the holding of the use-specific accessory, in particular the insemination gun, which thus does not fall to the ground, while providing hygiene and comfort for use.

The system for penetration, the remote screen and the use-specific accessory are thus manipulated by the operator with a single arm, which may be the right or left arm. The tool is ambidextrous.

The apparatus for vaginal penetration according to the invention may further comprise one or more of the following features, which may be combined together.

Advantageously, the electronic cell is comprised in the shaft.

Advantageously, the image transmission means comprise a connector for a connecting wire, or a means for wireless telecommunication.

The apparatus can thus be easily linked to an external screen.

In particular, the viewing means, such as a tube, may comprise a video system of videoscopic or fibroscopic type.

Advantageously, the viewing means may be of miniature camera type, where provided such a camera being fastened to an elongate support fastened, directly or indirectly, to the shaft and in the guide tube, advantageously so as to obtain focusing of the image on the axis of the front tip of the work tool, at a desired work distance ahead of the guide tube, presenting for example an inclination of 3° (degrees) relative to the axis of the artificial insemination apparatus in order to provide central vision and give the impression to the user that the camera is aligned along the working axis. The movement will thus seem more natural to the user.

This angle is defined relative to the distance of the viewing means with the front end of the guide tube, and at the same time in order for the center of vision to coincide with the center of the guide tube.

The camera may be fastened to the elongate support via two half-shells provided to cooperate together to be fastened together by closing on the elongate support so as to be fastened thereto.

Advantageously, the camera comprises the electronic cell.

Advantageously, the camera comprises image transmission means.

Advantageously, the work tool has graduations so as to enable a user to know the extent to which the front tip of the work tool has advanced relative to the shaft of the apparatus for penetration. Furthermore, at the time of the act of insemination, which is carried out with one hand, the graduation makes it possible to keep the advancement of the insemination gun within the cervix of the uterus centimeter by centimeter without risk for the animal. If necessary in case of emergency this same graduation enables the gun to be withdrawn very rapidly from the cervix of the uterus in order not to injure the animal. By virtue of this graduation, the penetration within the cervix is made gradually with full control of the act.

Advantageously, the work tool is an insemination gun, the insemination gun is comprised in a system comprising a gun extension to which it is fastened, the gun extension being formed to slide in the shaft along the axis of the shaft, to which is attached an injection needle or cannula of the gun comprising a straw containing the semen to discharge. Of course, the insemination gun may be replaced by a syringe for injecting an antibiotic, or any other injection device comprising a cannula, the gun extension then being adapted to fasten that a cannula of the syringe in which passes a piston of the syringe.

Advantageously, the gun extension is formed so that a push-button, or piston, of the insemination gun, can slide therein, for example inside the extension and along the axis of the extension.

Advantageously, the push-button is conformed to actuate a piston-rod of the insemination gun of which the front end is provided to move within the straw disposed within the injection needle and forward of the cannula to induce the discharge of the semen from the straw and from the injection needle.

More specifically and by way of example, concerning the insemination gun, the insemination gun comprises a rigid tubular body, or injection needle, to receive the straw filled with semen, and comprises a driving rod, or piston-rod, of the stopper of the straw, slideably mounted in the rigid tubular body. Before introduction of the straw into the rigid tubular body, the rod is removed or withdrawn to the maximum extent from the rigid tubular body by the proximal end (towards the back), that is to say by the end which is manipulated by the inseminator during the operation, then the straw is inserted into the rigid tubular body at its distal end (which is the opposite end to the proximal end, that is to say towards the front), the straw being inserted with the closest end of the tube to the stopper first. The straw is pushed into the rigid tubular body until the end of the tube encounters a shoulder forming a pushing-in stop. The straw is then in place in the rigid tubular body. The end of the straw tube that is the furthest from the stopper as well as a certain length of the tube starting from that end remain outside the rigid tubular body, that is to say that a certain part of the straw projects beyond the distal end of the rigid tubular body of the gun.

A sanitary sheath comprising a tube of which the inside diameter is such that the rigid tubular body of the gun can be inserted therein is then fitted.

At one end (the proximal end) the tube of the sanitary sheath is open and at the other end (distal end) the tube of the sanitary sheath comprises a turned back edge forming a hem on the inside. Inside the sheath a sliding sleeve member is disposed. The rigid tubular body of the gun, in which the straw was placed in advance, is inserted into the sheath by its open end with the straw first, the straw inserts into the sliding sleeve member and drives it. The insertion into the sheath ends when the sliding sleeve member and the straw come to bear against the hem-forming turned back edge situated at the distal end of the sheath (which is the opposite end to the open end of the sheath tube). The sheath is then fastened to the rigid tubular body of the gun, in general in the neighborhood of the proximal end of the sheath (open end of the tube) for example with a suitable ring. The straw tube is thus immobilized relative to the assembly formed by the tubular body of the gun and by the sanitary sheath fastened thereto. When the assembly formed by the sanitary sheath and the gun is in place, the piston-rod is used to make the stopper of the straw slide in order to eject, or discharge, the semen out from the straw tube and out from the sheath tube by the aperture surrounded by the hem-forming rim. The role of the sliding sleeve member is to provide liquid-tightness for the liquids between the straw tube and the sheath tube in order for the semen to be properly ejected out from the sheath (and not lost between the straw tube and the sheath tube).

Advantageously, the gun extension bears the graduations for measuring the advancement of the injection needle of the insemination gun, so as to know at the same time the advancement of the cannula in the uterus of the animal.

Advantageously, the graduations are inscribed on the gun extension and cooperate with members mounted in the shaft, such as spring-mounted balls in the shaft, to give a notch effect to the passing of each graduation, thus the user "feels" each of the graduations progressively as they cooperate with the members for the notch effect, enabling him thus to be more precise in his manipulation of the gun extension and thus in the advancement of the gun in the uterus.

Naturally, the members for the notch effect in cooperation with the graduations inscribed in the gun extension enable the gun extension to go backwards to return the gun back into the guide tube of the apparatus for vaginal penetration. Advantageously, they enable the gun extension to return without involvement of the user when the animal moves or contracts its internal muscles in the vicinity of the gun and more particularly of the front end of the cannula of the gun in order to maintain the animal's well-being, while preventing an inadvertent (undesired) return of the gun extension without movement or contraction of the animal nor any involvement of the user. Advantageously, and for this purpose, the members for the notch effect are mounted in the shaft using a mechanism which permits the disengagement of the members for the notch effect out of the graduations for a force orthogonal to the axis of the gun extension comprised between 4 Newtons and 8 Newtons, preferably substantially 6 Newtons.

It is understood that this notching may be produced for an extension of a syringe for injecting an antibiotic for example.

Advantageously, the shaft comprises at least one shaft which is preferably oblong extending along the axis of the shaft so as to lighten the shaft of the apparatus for vaginal penetration in order to make its use less constraining and improve the grip of the shaft, for example when one hand of the user cannot fully encircle the shaft when grasping the latter, the grasping thus not being satisfactory and leading to a risk of poor manipulation of the apparatus for vaginal penetration during the operations of artificial insemination.

Furthermore, the shaft opening makes it possible to slide the gun using a finger of the user, it being possible to perform the entire manipulation of the apparatus for vaginal penetration with a single hand in a simple way.

Lastly, the shaft opening enables better cleaning of the shaft after use of the apparatus.

The rear cell of the tool may comprise a battery incorporated into the shaft.

Advantageously, the guide tube may be made from an easily washable transparent material. It cleanliness is thus easily verified.

Advantageously, the guide tube, the viewing tube and a tube receiving the front tip of the work tool disposed therein, are fastened to the shaft by a mounting which may be of bayonet type providing reliability of connection as well as quick disassembly and easy washing.

Advantageously, the guide tube comprises at its base by the shaft, openings to the outside providing a mechanical ventilation system. Secretions in the uterus which come into that tube as well as the air present in the vagina are thus easily evacuated.

Advantageously, the assembly formed by the shaft and the guide tube, comprise a generally cylindrical shape. This design provides comfort to the user which is linked to ease of attaining the cervix of the uterus, and impossibility of snagging with the animal's tail, in particular cows, which avoids any risk of falling and destruction of the equipment by the animal.

Advantageously, the guide tube comprises a front face which is inclined to facilitate the penetration.

Advantageously, the apparatus for penetration may comprise a means for heating the gun, which enables semen to be kept up to temperature.

Advantageously, the viewing tube comprises a bent front end so as to obtain focusing of the image on the axis of the front tip of the work tool, at a desired work distance in front of the guide tube.

The invention also relates to a method of using an apparatus for vaginal penetration comprising any one of the preceding features, equipped with an insemination gun, comprising a first step while monitoring the view ahead of the guide tube, of passing through the vagina while inclining the shaft of the apparatus according to obstacles, then of illuminating the back of that vagina to locate the entrance of the cervix of the uterus, in order to dispose the front end of the guide tube in front of that cervix, then a second step while maintaining the shaft in that position, of pushing the insemination gun to make it enter the cervix of the uterus, and lastly of pushing the semen into that uterus.

The invention also relates to a method of using an apparatus for vaginal penetration comprising any one of the preceding features, equipped with a tool for depositing drugs, in particular antibiotics, comprising a first step while monitoring the view ahead of the guide tube, of passing through the vagina while inclining the shaft of the apparatus according to obstacles, then of illuminating the back of that vagina to locate the entrance of the cervix of the uterus, in order to dispose the front end of the guide tube in front of that cervix, then a second step while maintaining the shaft in that position, of injecting drugs into the uterus.

The invention also relates to a method of using an apparatus for vaginal penetration comprising any one of the preceding features, equipped with a tool for listening to sounds, comprising a first step while monitoring the view ahead of the guide tube, of passing through the vagina while inclining the shaft of the apparatus according to obstacles, then of illuminating the back of that vagina to locate the entrance of the cervix of the uterus, in order to dispose the front end of the guide tube in front of that cervix, then a second step while maintaining the shaft in that position, of listening to sounds emitted beyond the cervix.

The invention also relates to a method of using an apparatus for vaginal penetration comprising any one of the preceding features, equipped with a photographic tool, comprising a first step while monitoring the view ahead of the guide tube, of passing through the vagina while inclining the shaft of the apparatus according to obstacles, then of illuminating the back of that vagina to locate the entrance of the cervix of the uterus, in order to dispose the front end of the guide tube in front of that cervix, then a second step while maintaining the shaft in that position, of photographing that cervix. Annotations and other items may be linked to the collected images.

The invention lastly relates to a method of using an apparatus for vaginal penetration comprising any one of the preceding features, equipped with a tool for sampling internal substances, comprising a first step while monitoring the view ahead of the guide tube, of passing through the vagina while inclining the shaft of the apparatus according to obstacles, then of illuminating the back of that vagina to locate the entrance of the cervix of the uterus, in order to dispose the front end of the guide tube in front of that cervix, then a second step while maintaining the shaft in that position, of sampling substances.

The invention will be better understood and other features and advantages will appear more clearly on reading the following description given by way of example, with reference to the accompanying drawings in which.

Figure 1A:
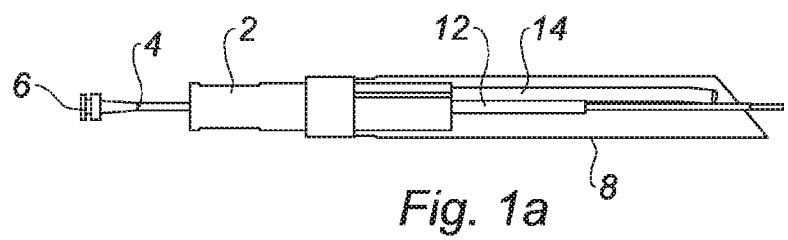
FIGS. 1a and 1b are overall views of an apparatus for penetration according to the invention, comprising an insemination gun.
Figure 1B:
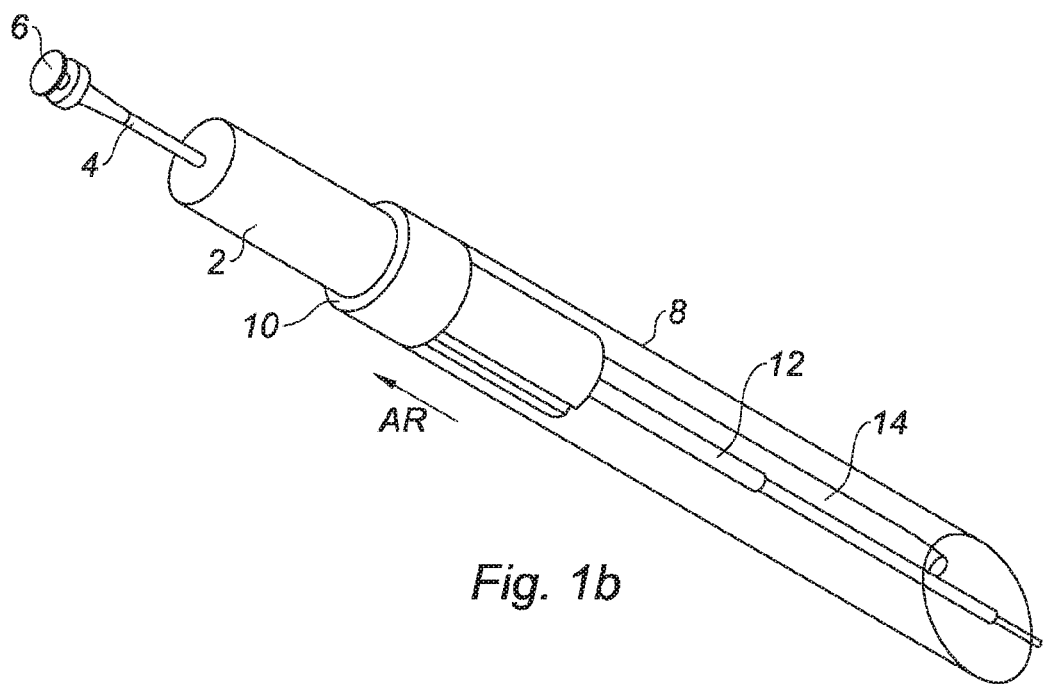

FIGS. 1a and 1b present an apparatus for penetration forming an assembly comprising an elongate shape which is substantially cylindrical, presenting towards the back indicated by the arrow "AR", a handling shaft 2 receiving along its axis an injection gun 4 sliding therein, comprising an injection needle, or rod of the insemination gun containing the straw, ending at the rear with a push-button 6, and at the front with a tip.

The shaft is extended forward by a guide tube made from transparent plastic material 8, which is fastened in the middle of that shaft by an intermediate clamping ring 10. The guide tube 8 comprises internally an axial tube 12 surrounding the front tip of the gun, and next to an endoscopic tube 14 of a video system. The diameter of this guide tube 8 is within the dimensions which respect the well-being of the animal, and facilitate penetration, and especially have a smaller diameter than those already known so as to be suitable for the majority of the animals it is wished to inseminate.

By way of example, in the case of cows, the diameter is preferably comprised between 30 millimeters and 43 millimeters, the diameter is preferably substantially 36 millimeters and can thus be suitable for practically all bovine livestock while respecting their well-being and in order to improve the conditions of insemination, in particular of heifers, whereas the known apparatuses for vaginal penetration could have a diameter of 4 centimeters or 5 centimeters. In the case for an application for ovine livestock, the diameter could be further reduced.

Figure 2:
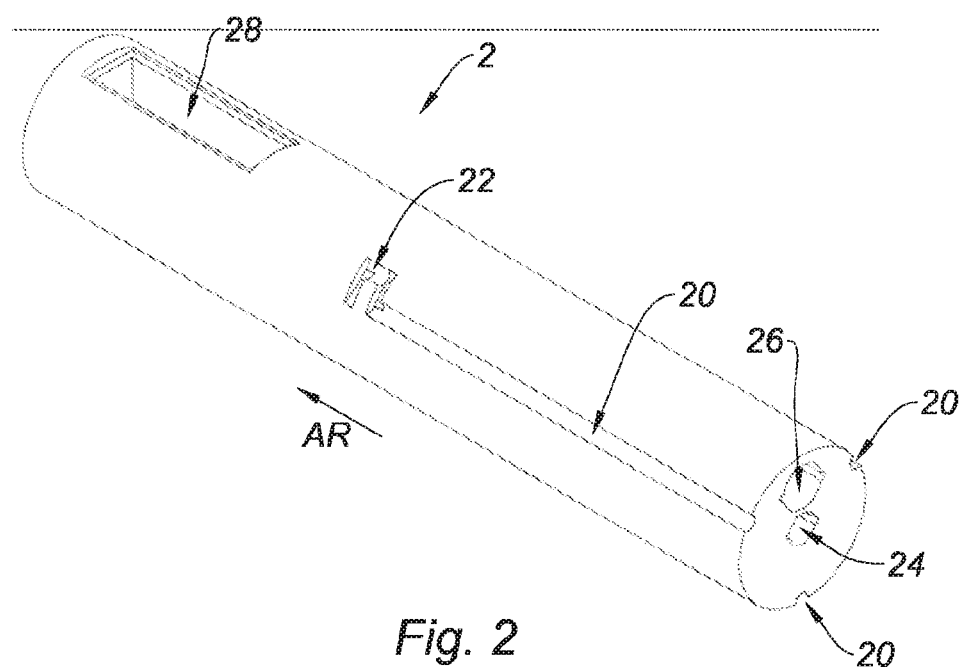
FIG. 2 is a detail view of the shaft of that apparatus.

FIG. 2 presents the shaft 2 comprising a cylindrical outside contour, presenting three longitudinal grooves 20 starting from the front, which each terminate substantially in the middle of that shaft by a groove 22 forming a small crenel comprising a first transverse part, a short longitudinal part and a second transverse part parallel to the first.

The shaft 2 has an axial bore 24 which passes all the way through it.

The front part of the axial bore 24 comprises over a small length a greater diameter comprising two longitudinal grooves which each end at the rear with a short transverse groove along a circle arc, in order to receive with a close fit the rear part of the gun tube, and to fasten it with a bayonet-type mounting.

The shaft 2 comprises a second longitudinal bore 26 which is offset relative to the axis, which starts from the front and opens towards the rear in an elongate cavity 28 open on one side of that shaft, provided to contain a rear cell of the endoscope receiving the images coming from the end of the viewing tube 14.

The rear cell of the apparatus can receive electrical energy by an external cable, connected for example to a tablet or a smartphone, or intelligent telephone, performing the display. As a variant, a battery may be incorporated in the shaft 2 to supply that rear cell.

The cavity 28 is provided to receive a cover not shown, which is fitted closely to the outside cylindrical surface, in order to close it to protect the interior of the cell of the video system while presenting an outside contour of the shaft 2 which is smooth.

As for the axial bore 24, the offset bore 26 comprises on a front part two longitudinal grooves which each terminate at the rear with a transverse groove, to receive the endoscope tube 14 and fasten it by a bayonet type mounting.

Figure 3:
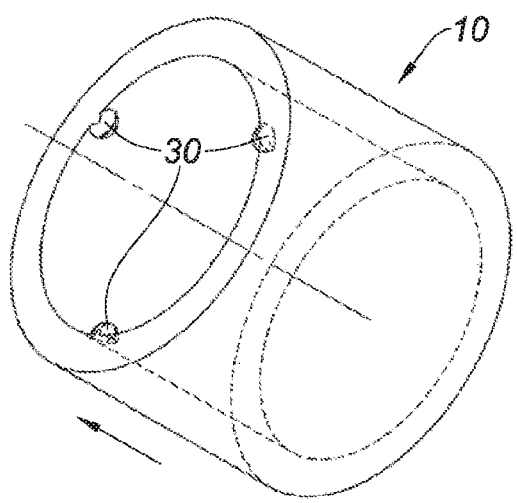
FIG. 3 is a detail view of the intermediate ring.

FIG. 3 presents the cylindrical intermediate ring 10, provided to receive the guide tube 8 which is bonded thereto.

The intermediate ring 10 comprises an inside diameter closely fitting the outside contour of the shaft 2, which has three lugs 30 jutting outwardly, which are provided each to enter a longitudinal outside groove 20 of that shaft starting from the front.

Once in the rear position, the assembly formed by the guide tube 8 and its intermediate ring 10 fastened within, is maneuvered to pass each lug 30 into the crenel 22, by turning it, withdrawing it rearwardly, then turning it in the opposite direction. An assembly of the guide tube 8 to the shaft 2 is thus produced that is quick and rendered secure, which provides precise positioning.

Figure 4:
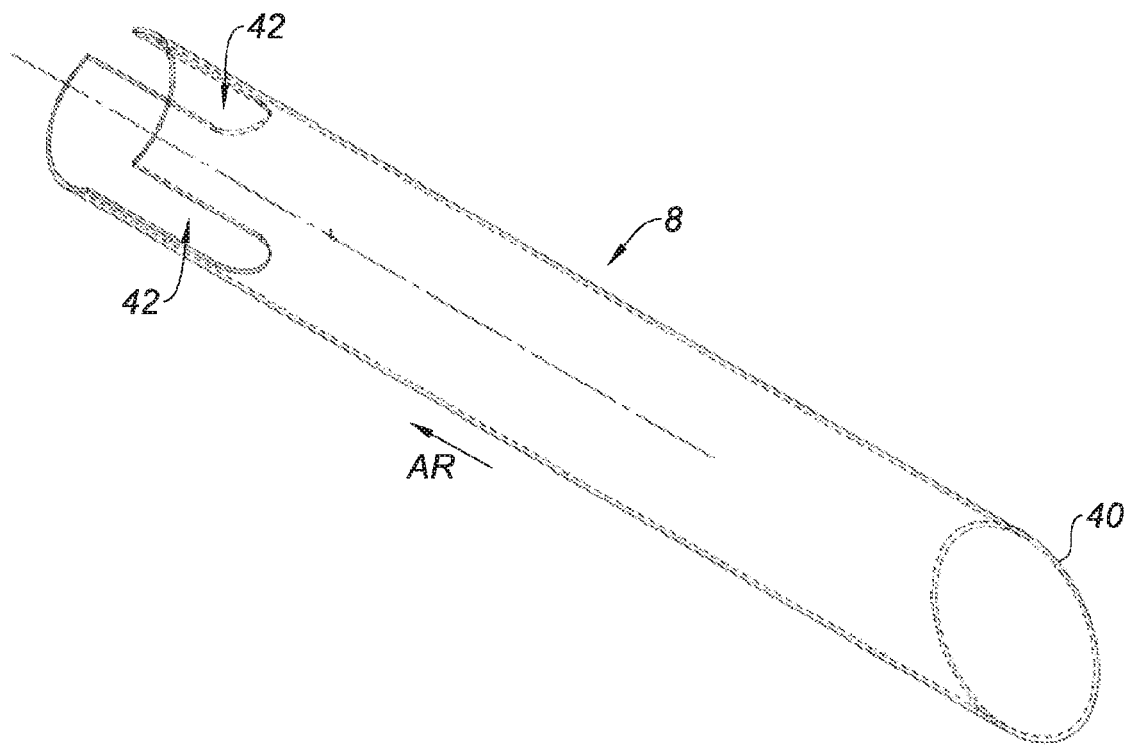
FIG. 4 is a detail view of the guide tube.

FIG. 4 presents the guide tube 8 made from transparent plastic material such as plexiglas, comprising an inclined front face 40 facilitating the advancement towards the uterine cervix, and a rear end having a close fit in the intermediate ring 10, which is clamped and bonded therein.

The rear part of the guide tube 8 comprises two opposite longitudinal slots 42 which open towards the rear. The front part of each slot 42 comes in front of the intermediate ring 10, so as to form two opposite openings when the guide tube 8 is mounted on the shaft 2.

When the guide tube is inserted into the animal, the openings of the two slots 42 enable a passage of air to be created which communicates with the internal spaces of the animal, and to evacuate secretions to be found in the vagina and coming into that tube at the time of its insertion. By inclining the shaft downwardly these secretions are enabled to slide along the tube, and to exit by one of the slots 42.

The transparent material of the guide tube 8 enables its internal state of cleanliness to be monitored during the operations, and afterwards when it is washed and disinfected.

Figure 5:
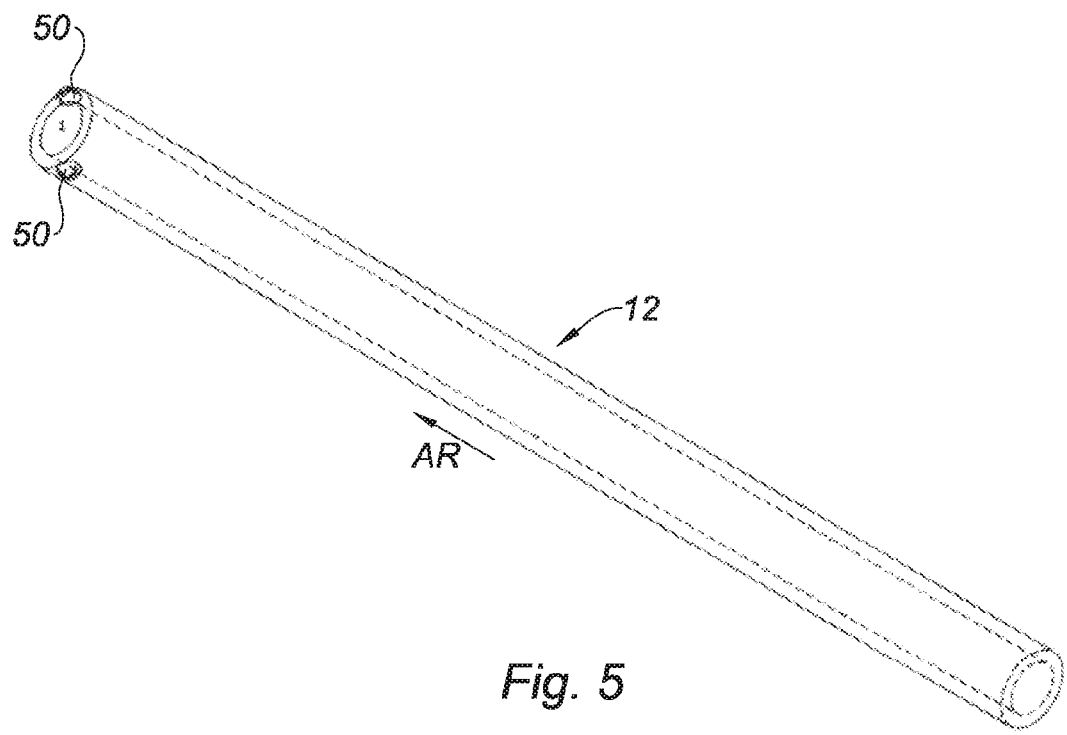
FIG. 5 is a detail view of the gun tube.

FIG. 5 presents the gun tube 12 comprising a uniform diameter, its rear part coming to have a close fit in the front part of the axial bore 24 of the shaft 2. The rear end of the gun tube 12 has two outwardly turned diametrically opposite lugs 50 which each have a close fit in a longitudinal slot of that axial bore 24.

Once it has been pushed into its rearward position, the gun tube 12 is rotated in order to dispose the lugs 50 in the transverse grooves of the shaft 2, to form a bayonet-type fastener which is simple, fast and effective. The front end of the gun tube 12 comes substantially to the middle of the length of the guide tube 8 jutting forward of the shaft 2.

Figure 6:
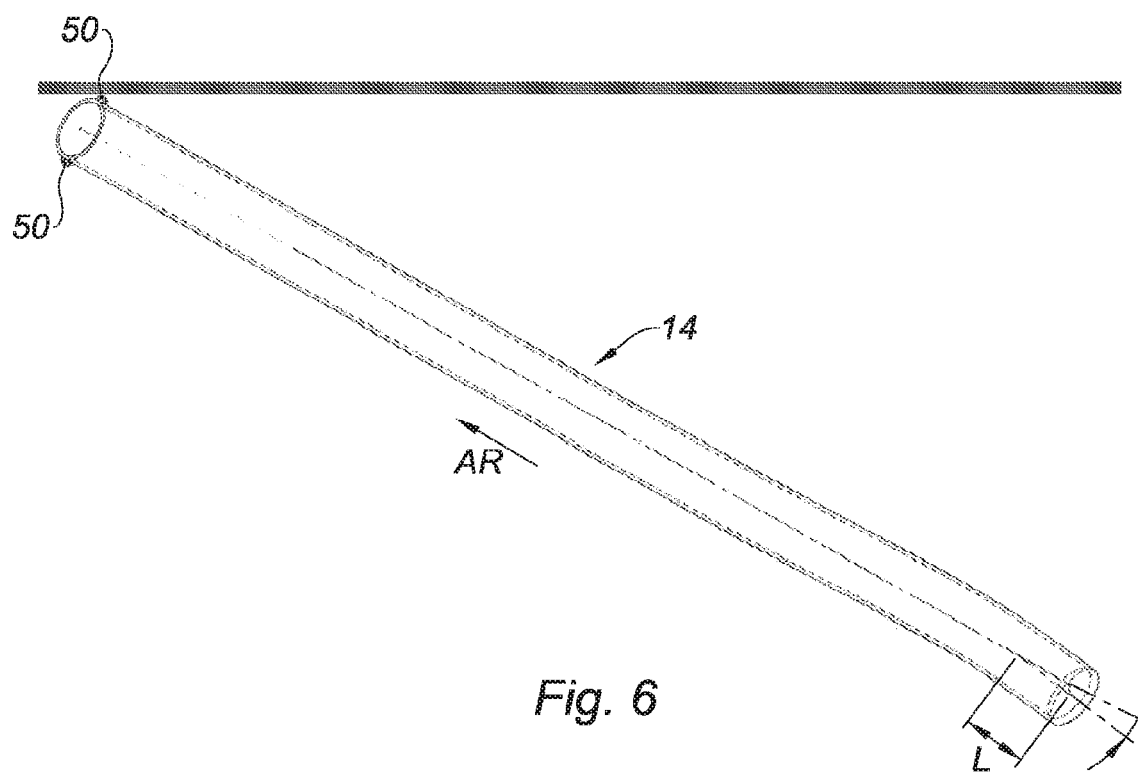
FIG. 6 is a detail view of the viewing tube.

FIG. 6 presents the viewing tube 14 comprising as for the gun tube 12, a uniform diameter, and a rear part having a close fit in the front part of the offset bore 26 of the shaft 2, which is equipped at its front end with two lugs 50 in order to form a bayonet-type mounting on that shaft.

The front end of the viewing tube 14 which at the same time provides lighting, given in particular by cells of "LED" type, as well as a view forward, stops slightly short of the front face 40 of the guide tube 8 which thus protects that end.

The front part of the viewing tube 14 is on a small length L, bent through an angle $\alpha$ so as to obtain focusing of the image on the axis of the apparatus at a desired work distance forward of that tube, which is located substantially at the tip of the injection needle when it is advanced. The depositing of the semen by the tip of the needle can thus be monitored.

Generally for the use of another work tool in the apparatus for penetration, it is possible in the same way to monitor the working of the tip.

The viewing tube 14 may comprise different viewing systems. It is possible in particular to use a fibroscopic system performing the transmission of images by optic fibers which send the light forward, and return the images to the rear cell situated in the cavity 28 of the shaft 2. As a variant a video system may be used, the end of the viewing tube 14 comprising a lighting means, as well as a photosensitive sensor, for example of the "CCD" type.

The focusing of the viewing means is made substantially on the tip of the gun 4 which is located in its forward position, to be able to precisely follow the depositing of the semen which is located at that tip.

The shaft 2 may comprise an on-button of the video system, which is not represented in the drawings. The rear cell of the video system communicates with the display system which is dissociated from the apparatus for penetration, by a connecting wire, using for example a "USB" type connector located on the shaft, or by a wireless connection, for example using radio communication of the "Bluetooth" type.

Thus, with a radio or "USB" wired connection, a system is thus obtained which is adapted to numerous tools on the market. A programmed software application may be installed by downloading on most apparatuses on the market. This application provides the communication between the remote apparatus and the radio system. The application enables the user to entre a variable number of items of information on the action carried out by the user and the animal concerned. The data recorded by this application may be synchronized with a database instantaneously or at a later stage. It will be possible to define and develop services facilitating the live and well-being of the user and of the animal, progressively with usages.

In the case of a wireless connection, the shaft 2 contains the electronics for control of the lighting and viewing means, as well as an autonomous electrical supply.

The display system may in particular use a mobile telephone or a tablet. It may in particular use a "Smartphone" type apparatus disposed for example in a fluid-tight sheath comprising fastening means, in particular a strap comprising a quick fastener of the "Velcro" type for fastening it to the user's arm.

The display system may also use any other viewing system, in particular a system integrated into spectacles with radio communication of "Bluetooth" type.

In this way the operator can follow the advancement of the front end of the apparatus on a stable, clean screen, while guiding that end by inclinations of the shaft in order to facilitate the passage between the various tissues of the internal cavities which appear.

The images obtained, photographs or films, may be stored in a memory then transferred into a database, which enables them to be brought out later to monitor change in the animal.

For example by referencing the type of straw used for an insemination, data may be stored on the operations carried out on each animal.

These images may also be transmitted, in particular via the Internet, to an outside person such as a vet, to perform a diagnosis, or monitor the state of health of the animals.

The manner of operating the apparatus is as follows. The viewing means and the remote screen make it possible to track the path within the vagina of the apparatus for vaginal penetration, then to illuminate the back of the vagina to locate the entrance to the cervix of the uterus, in order to place the front end of the guide tube in front of the cervix of the uterus. Next, the operator, while holding the shaft in that position, pushes the insemination gun (4) with that same hand straddling the shaft and the insemination gun, the extension of the insemination gun depending on the case, to make it enter the cervix to reach the uterine body, and lastly pushes the contents of the straw into that uterus still with the same hand then straddling the shaft and the push-button, then operating in the manner of a piston.

During the operation according to the internal state observed with the viewing, in particular the dilation of the cervix, the presence of mucus or the cleanliness of that mucus, the operator can decide whether or not to inject semen. The chances of success of the insemination are thus strongly ensured.

As work tool the apparatus for penetration may use different known types of insemination gun, or tools for depositing various products, in particular antibiotics.

Accessories may be provided to adapt the apparatus for penetration to different uses. In particular there may be provided in the shaft of the apparatus a preheating system for the gun, using for example an electrical resistance, or a suitable heating or insulating substance, in order to avoid thermal disparities between the defrosting of the semen and its insertion, which reduce its activity.

As work tool a tool for listening to sounds beyond the cervix of the uterus may be used, making it possible, by placing the front end of the guide tube 8 in front of that cervix, to listen to sounds emitted beyond.

A tool for photographing the cervix of the uterus may also be used. Furthermore a tool for sampling substances may be used, to perform in particular a cytobiological examination by sampling.

After an operation the different tubes of the apparatus for penetration, which are all fastened to the shaft by the bayonet-type quick assembly, are easily disassembled for complete washing of the apparatus.

It is to be added that the apparatus for vaginal penetration may of course receive tools that already exist if this is useful and that only minor modifications for the adaptation of the apparatus are to be made for this purpose and without any difficulty whatsoever.

In a variant not illustrated, a telescopic mechanism of actuators is described also enabling the single-handed utilization of the apparatus for penetration. In this variant, when the apparatus for penetration has been inserted as far as the cervix of the uterus using a handling shaft (2), the insemination gun, and more specifically an extension of the insemination gun, slides within the shaft (2) and when lastly, and in a conventional manner this time, the content of the straw placed within and to the front of the gun has been discharged using the push-button (6) operating in the same way as a piston, that is to say sliding within the body of the gun forward of the gun to push the content of the straw into the uterus. Preferably, and in a conventional manner, the piston has a smaller diameter than the diameter of the gun so as to slide without jolting within the actual interior of the gun and the piston then makes it possible to push a stopper located in the straw which itself pushes the content of the straw, that is to say semen, into the uterus under the action of the piston. The stopper may have a conventional constitution comprising for example three successive strata inside and along the straw of which a first is of wadding and a second of gel and a third again of wadding. The stopper is initially, prior to any operation directed to discharging semen, disposed at the rear of the straw that is to say in a part of the straw which is the closest to the shaft of the apparatus for penetration. With the piston pushing the stopper towards the front of the straw, the wadding in contact with the piston enables the gel and the third stratum of wadding to be pushed in optimal manner within the straw.

Of course, this last variant not illustrated having a telescopic mechanism is applicable for any type of work tool, by way of non-limiting example a tool for depositing drugs, a tool for listening to sounds, a tool for taking photographs or a tool for sampling internal substances.

The telescopic mechanism comprises at least the shaft and the gun extension, and optionally the push-button, which is optional on the tool for listening to sounds for example.

Lastly, in a variant not illustrated, the push-button may be actuated if necessary by a piston extension, which is an extension of the push-button, sliding inside the gun extension, this piston extension, when it is useful, forms part of the telescopic mechanism.

The invention claimed is:

1. A work assembly comprising:
   an apparatus for aiding in vaginal penetration comprising: a handling shaft, a guide tube extending the shaft to form a compact assembly, and a video viewing tube, comprising lighting at a front end of the video viewing tube; the video viewing tube being received in the guide tube; the shaft comprising a video system rear cell having an image transmitter for transmitting to a remote screen images coming from the video viewing tube; and
   a work tool received in said apparatus, said work tool being an insemination gun configured for penetrating a vagina to reach a cervix of a uterus of an animal, said work tool passing through the shaft, in relation to which the work tool is slidable, the work tool comprises a front tip, and is movable between a position in which the front tip is received in the guide tube and a position in which the front tip projects forward from the guide tube.

2. A work assembly according to claim 1, wherein the front end of the viewing tube provides at the same time lighting as well as view forward.

3. A work assembly according to claim 1, wherein the image transmitter comprises a connector for a connecting wire.

4. A work assembly according to claim 1, wherein the rear cell of the apparatus comprises a battery integrated into the shaft.

5. A work assembly according to claim 1, wherein the guide tube is made from an easily washable transparent material.

6. A work assembly according to claim 1, wherein the guide tube, the video viewing tube, and another tube receiving the front tip of the work tool disposed therein, are fastened to the shaft by a bayonet type mounting.

7. A work assembly according to claim 1, wherein the guide tube has a base and comprises openings to outside the guide tube at the base by the shaft.

8. A work assembly according to claim 1, wherein the compact assembly formed by the shaft and the guide tube comprise a generally cylindrical shape.

9. A work assembly according to claim 1, comprising a telescopic mechanism comprising at least the shaft and a work tool extension.

10. A work assembly according to claim 1, wherein the guide tube comprises a front face which is inclined.

11. A work assembly according to claim 1, comprising a heater of the work tool.

12. A work assembly according to claim 1, wherein the video viewing tube is oriented so as to obtain focusing of an image on an axis of the front tip of the work tool, at a desired work distance in front of the guide tube.

13. An assembly according to claim 1, wherein the viewing tube comprises a bent end so as to obtain focusing of an image on an axis of the front tip of the work tool, at a desired work distance in front of the guide tube.

14. A set comprising:
a work assembly according to claim 1, in which the work tool is the insemination gun, and
an alternative work tool into be received in the apparatus, the alternative work tool being a tool for depositing drugs.

15. A set comprising:
a work assembly according to claim 1, in which the work tool is the insemination gun, and
an alternative work tool to be received in the apparatus, the alternative work tool being a tool for listening to sounds.

16. A set comprising:
a work assembly according to claim 1, in which the work tool is the insemination gun, and
an alternative work tool to be received in the apparatus, the alternative work tool being a photographic tool.

17. A set comprising:
a work assembly according to claim 1, in which the work tool is the insemination gun, and
an alternative work tool to be received in the apparatus, the alternative work tool being a tool for sampling internal substances.

18. A work assembly according to claim 1, wherein the viewing tube includes a video system of videoscopic or fibroscopic type.

19. A work assembly according to claim 1, wherein the guide tube comprises internally, next to the viewing tube, a tube configured for receiving the front tip of the work tool disposed therein.

20. A work assembly according to claim 3, wherein said connector is a USB connector.

21. A work assembly according to claim 1, wherein the image transmitter comprises a wireless telecommunication transmitter.

22. A work assembly according to claim 1, wherein the rear cell of the apparatus is configured for receiving electrical energy by an external cable connected to a tablet or a smartphone performing display.

23. A non-surgical method of using an assembly according to claim 1, comprising:
a first step of:
monitoring a view ahead of the guide tube
passing through a vagina,
inclining the shaft of the apparatus according to obstacles, and then
illuminating a back of said vagina to locate an entrance of a cervix of a uterus, in order to dispose a front end of the guide tube in front of said cervix; and
then
a second step of:
maintaining the shaft in a fixed position,
pushing the insemination gun to make it enter the cervix of the uterus, and lastly,
pushing semen into said uterus.

* * * * *